United States Patent [19]

Pinchuk

[11] Patent Number: 5,147,725
[45] Date of Patent: Sep. 15, 1992

[54] METHOD FOR BONDING SILICONE RUBBER AND POLYURETHANE MATERIALS AND ARTICLES MANUFACTURED THEREBY

[75] Inventor: Leonard Pinchuk, Miami, Fla.

[73] Assignee: Corvita Corporation, Miami, Fla.

[21] Appl. No.: 548,285

[22] Filed: Jul. 3, 1990

[51] Int. Cl.$^5$ .................. B32B 27/00; B32B 27/40
[52] U.S. Cl. .................. 428/425.5; 427/387; 427/393.5; 428/447
[58] Field of Search .............. 428/425.5, 447; 427/387, 393.5

[56] References Cited

U.S. PATENT DOCUMENTS

| | | | |
|---|---|---|---|
| 4,595,610 | 6/1986 | Fey et al. | 427/387 |
| 4,681,808 | 7/1987 | Lefler, III | 428/425.5 |
| 4,739,013 | 4/1988 | Pinchuk | 525/101 |
| 4,814,231 | 3/1989 | Onohara et al. | 428/425.5 |
| 4,847,120 | 7/1989 | Gent | 427/387 |

*Primary Examiner*—Michael Lusignan
*Attorney, Agent, or Firm*—Lockwood, Alex, Fitzgibbon & Cummings

[57] ABSTRACT

A method for applying a silicone rubber material to polyurethane is described wherein a previously processed polyurethane material can be strongly bonded to a silicone rubber material. The silicone rubber material is applied to the polyurethane in a solution and is preferably an acetoxyterminated silicone material, a halogen-terminated silicone material or a combination thereof. The polyurethane and the silicone rubber material are heated at a temperature above about 70° C. to bond the two materials together more strongly than would otherwise occur in the absence of heat.

19 Claims, No Drawings

METHOD FOR BONDING SILICONE RUBBER AND POLYURETHANE MATERIALS AND ARTICLES MANUFACTURED THEREBY

BACKGROUND AND SUMMARY OF THE INVENTION

This invention relates to methods for bonding silicone rubber materials directly to polyurethane materials without the use of adhesives and to articles manufactured by such methods. Polyurethane molecules having terminal hydroxyl or isocyanate groups will bond with silicone rubber materials and specifically with silicone rubber materials having alkoxy or halogen moieties associated with one or more of the silicon atoms in the rubber material. Polyurethane materials which have been stored for extended periods of time may be heat-treated prior to contacting the polyurethane with the silicone rubber material. Such heat treatment conditions the polyurethane to form a lasting and strong bond with the silicone material.

Treatment of various polymers by coating, for example, with silicone rubber materials is known. Such a treatment is described in my U.S. Pat. No. 4,851,009, the disclosure of which is incorporated by reference herein. Coating treatments such as those described in the aforementioned letters patent are useful and necessary in minimizing and even preventing the cracking which occurs in prostheses made of polymeric materials, such as polyurethane, following implantation in a living body and after extended in vivo use.

The treatment of urethane materials with silicone rubber materials also has applications in the manufacture of various articles which are not intended to be subjected to substantial or continuous in vivo use. Where such articles will not be implanted in a living body, it is not necessary to fully coat the article because cracking of the polymer is not an expected problem. However, it may be desirable to manufacture such articles out of a combination of materials such as polyurethane and silicone rubber materials in a manner whereby the silicone rubber is strongly bonded to the polyurethane to thereby eliminate the need for and the use of an adhesive in securing the component pieces of such objects together. The art has generally failed to provide such a method where previously manufactured polyurethane materials are to be bonded to silicone rubber materials and especially where the polyurethane material was originally prepared a substantial amount of time in advance of bonding to the silicone rubber material.

The present invention provides a method for manufacturing articles out of dissimilar materials such as polyurethanes and silicone rubber materials. Specifically, isocyanate- and/or hydroxy-terminated polyurethanes can be directly bonded to alkoxy- or halogen-terminated silicone rubber materials to bond the silicone material to the polyurethane and vice versa. Heating of the polyurethane will condition the surface of the polyurethane to render it more receptive to bonding with the rubber material. Time and temperature requirements for such heating generally depends on the particular urethane its glass transition temperatures and the amount of time which has lapsed since that urethane was originally processed (e.g. extruded).

The method of the present invention has applications in the manufacture of a variety of articles made from the types of materials described herein. For example, medical or surgical devices such as suture collars, vascular grafts, pacemaker lead insulators, heart valves, sutures and the like. Other applications such as silicone-coated polyurethane foam roof insulators, for example, are also contemplated.

It is accordingly an object of the present invention to provide a method for the manufacture of articles made from one or more polyurethanes and one or more silicone rubber materials.

It is another object of the present invention to provide a method for the manufacture of articles made from one or more polyurethane materials and one or more silicone rubber materials wherein the polyurethane material is heat treated to condition its surface for bonding to the silicone rubber material.

It is still another object of the present invention to provide articles manufactured according to the aforementioned method.

These and other objects and advantages of the present invention will be apparent to those skilled in the art upon consideration of the remainder of the disclosure.

DETAILED DESCRIPTION OF THE INVENTION

The present invention provides a method for bonding urethane materials to silicone rubber materials whereby previously prepared polyurethane materials can be further treated with an alkoxy- or halogen- terminated silicone material to provide an end product wherein the silicone rubber material is bonded to the polyurethane base material or substrate in a strong bond which readily resists a forced separation between the urethane and silicone materials.

In the manufacture of objects and devices made with a polyurethane, advantages are often realized by coating the polyurethane with a silicone rubber type of material. Medical devices such as vascular grafts, implanted catheters and the like must be made to withstand extended periods of exposure to the conditions inherent in in vivo use of such devices. Such devices, when made with a polyurethane, are rendered more resistant to degradation generally when coated with a silicone rubber type of material. The formation of such silicone rubber-coated devices has traditionally required coating of the polyurethane substrate or base material within a specified amount of time following the manufacture or formation of the polyurethane in order to achieve a strong bond between the urethane and the silicone material. The present invention provides a method for the treatment or coating of polyurethane materials following substantial periods of time after processing or formation of the polyurethane base material. In this manner, the polyurethane base materials can be manufactured and stored for extended periods of time and, when needed or desired, the base material can be coated with a silicone rubber material to form the same cohesive bond which is experienced when the polyurethane materials are coated shortly after the formation of the polyurethane substrate.

In a method according to the principals of the present invention, a polyurethane material is treated with a solution containing an alkoxy- or halogen- terminated silicone rubber material. The polyurethane material is heated to a temperature above 70° C. and preferably at a temperature between about 100° C. and about 130° C. Heating of the polyurethane may be accomplished either immediately before or preferably after being treated with the silicone rubber material. The silicone rubber material is cured and bonded to the polyurethane. After a set period of time which may vary from less than about one minute up to about thirty minutes or more, the silicone-coated urethane is cooled and inspected and may then be further processed in a manner consistent with its intended end use.

With more particular reference to a preferred embodiment, a base material made with a polyurethane is provided which can be one or more commercially available products. When the end product is to be used specifically in medical related applications such as implanted vascular grafts and the like, the polyurethane is preferably selected from a family of polyurethane polymers containing the basic components of a diisocyanate, a macroglycol and a chain extender. More specifically, the polyurethane for use in medical applications will be selected from those polyurethanes having macroglycols in the form of polyester glycols, polyether glycols and polycarbonate glycols. Especially in the case of polyurethanes containing polyether glycols and polyester glycols, silicone rubber coating of such polymers is desirable to prevent cracking, even upon implantation in a living body.

The polyurethane material is dip coated or passed through a bath of an alkoxy- or halogen- terminated silicone. Most preferably, the silicone rubber material is acetoxy terminated. Preferably, the bath will contain an acetoxy terminated silicone in an amount of about 10% by weight dissolved in a solvent mixture. A suitable solvent for this type of bath is a mixture of a fluorocarbon such as that available under the trademark Freon TF, for example, and 1,1,1-trichloroethane. Most preferably, the solvent will contain approximately 90% fluorinated hydrocarbon and 10% 1,1,1-trichloroethane. The coated polyurethane material is then placed in an oven and exposed to an elevated temperature for a period of time sufficient to cure the silicone rubber material and bind it to the urethane. Suitable temperatures for the heat treatment of the coated polyurethane is dependent upon the glass transition temperatures of the polyurethane and can vary from between about 70° C. up to the melting point of the polyurethane. Most preferably, the temperature will be between about 100° C. and about 130° C. A suitable time for the heat treatment of the coated polyurethane can also vary depending upon the specific materials used and their geometries and the thickness of the coating and the substrate. However, a typical period of time for heat treating the polyurethane is about 10 minutes in those cases where an acetoxy-terminated silicone rubber material is coated over a polyurethane such as a polyester polyurethane or a polyether polyurethane, for example. Following heat treatment, the article can be further processed, if desired, in a manner which is consistent with its intended use. If desired, the polyurethane can be heat treated prior to being coated with the silicone-rubber material. The silicone rubber can be applied at room temperature immediately after the polyurethane has been heated. The rubber material can then be cured at room temperature.

With more particular reference to the type of silicone rubber material used, commercially available silicone rubber materials have been satisfactory. Such materials include room temperature vulcanizing silicone rubber materials such as those available from Dow Corning Corporation, for example. In general, the silicone material is preferably an alkoxy- or a halogen-terminated silicone rubber and, most preferably, is an acetoxy-terminated silicone rubber. Suitable silicone rubber type components, especially those used in the crack preventative treatment of implantable medical devices, are those described in my U.S. Pat. No. 4,851,009, the disclosure of which is incorporated by reference herein.

EXAMPLE 1

Cardiac pacemaker lead insulator tubing is manufactured in accordance with the invention to protect it from in vivo cracking following implantation. Polyurethane tubing made from commercially available polyurethane such as Dow Chemical, Pellethane 80AE is extruded and spooled in a known manner and is stored until needed. Treatment of the polyurethane tubing is accomplished by pulling the urethane tubing off of the spool in a continuous process and through a bath of an acetoxy- terminated silicone such as Medical Adhesive A by Dow Corning Corporation at a concentration of about 10% by weight. The acetoxy terminated silicone is dissolved in a solvent made of a mixture of 90% of a fluorinated hydrocarbon commercially available under the trademark Freon TF available from E. I. DuPont de Nemours & Co. and 10% 1,1,1-trichloroethane. The tubing is pulled through the bath and into an oven where it is heated at 120° C. for approximately 2 minutes while hot air is blown directly on the silicone/polyurethane device. The silicone material is allowed to cure while it is bonding to the urethane at the elevated temperature within the oven. The tubing is then cooled, inspected and cut to required lengths for use as pacemaker lead insulator tubing.

EXAMPLE 2

Two spools of the tubing described in Example 1 are coated in the silicone bath simultaneously and then aligned in a side by side relationship so that two lengths of urethane tubing are joined as a single unit by adhesion between the respective acetoxy silicone coatings. Following heating and curing of the silicone rubber material, the two lengths of polyurethane tubing are secured together and are strongly bonded to the silicone rubber.

EXAMPLE 3

Silicone pacemaker lead tines are bonded to a polyurethane pacer lead insulator in the following manner: The silicone tines are manufactured in a conventional manner by compression or injection molding with a suitable silicone rubber such as a platinum cured liquid silicone rubber or a peroxide cured silicone rubber or a room temperature vulcanized silicone rubber. The tines are removed from the mold and coated on the lumen side with an acetoxy terminated silicone rubber such as Dow Corning's Medical Adhesive A. Prior to curing the adhesive, the tines with the still wet adhesive are placed in position over the polyurethane insulator, the assembly is then placed in an oven for 10 min at 120° C. when the adhesive is bound to both the silicone tines and the urethane lead. It can be appreciated that polyurethane tines can be bound to a polyurethane insulator in a similar manner. Similarly, polyurethane tines can be bound to a silicone insulator in the same manner.

The general range of temperatures for heating a silicone treated polyurethane material will vary from less than 5 minutes up to several hours depending upon the type of urethane used, its geometry, thickness and the amount of time which has elapsed since the urethane was initially processed. Temperatures can vary from between the second glass transition temperature of about 70° C. up to the melting point of the polyurethane material although room temperature curing of the silicone rubber material is also contemplated within the scope of the invention. In general, heating the polyurethane for 10 minutes at 125° C. will be satisfactory for bonding most room temperature vulcanizing rubber materials wherein the silicone material is acetoxy terminated. A thicker silicone coating can be part cured after the initial heat treatment at room temperature and humidity.

Applications of the bonding technique include the aforementioned medical devices which include sutures, tubing for cardiac pacemaker lead insulators, balloon catheters such as those used in cardiac angioplasty, for example. In this regard, a silicone catheter can be bonded directly to a polyurethane balloon or, conversely, a soft silicone material can be manufactured as a silicone tip for a polyurethane catheter. Other medical applications include heart valves, vascular grafts, various indwelling catheters, artificial ureters and the like. Non-medical applications are also contemplated and include the manufacture of silicone coated polyurethane foam roof coatings, for example.

While a preferred embodiment of the present invention has been described, it will be appreciated by those skilled in the art that changes or modifications can be made to the described method without departing from the true spirit and scope of the invention as defined in the claims.

I claim:

1. A method for applying a silicone rubber material, comprising:
   supplying a base material having an exposed surface which includes a polyurethane;
   applying an uncured silicone rubber material to said exposed polyurethane surface of the base material, said silicone rubber material being an acetoxy-terminated siloxane, a halogenterminated siloxane or a combination thereof said acetoxy and halogen moieties being bonded directly to silicon in said rubber material;
   heating said base material at a temperature above about 70° C. to condition said polyurethane surface for bonding said silicone rubber material to said polyurethane; and
   curing said silicone rubber material;
   whereby said heating of said base material provides a bond between said silicone rubber material and said polyurethane which is stronger than a bond which occurs between said polyurethane and said silicone rubber material in the absence of said heating step.

2. The method as defined in claim 1 wherein said heating of at least said base material is accomplished by heating above the second glass transition temperature of said polyurethane.

3. The method as defined in claim 1 wherein said silicone rubber material is applied to said base material as a solution consisting essentially of about 10% by weight of said silicone rubber material in a solvent, said solvent being formulated as a blend of about 90% fluorinated hydrocarbon and about 10% 1,1,1-trichloroethane.

4. The method as defined in claim 1 wherein said heating of said base material and said silicone rubber material is carried out at a temperature between about 100° C. and about 130° C. for a period of time between about 0.5 minutes and about 15 minutes.

5. The method as defined in claim 1 wherein said curing of said silicone rubber material is accomplished during said heating of said base material and said silicone rubber material.

6. The method as defined in claim 1 further comprising:
   blowing air on said base material and silicone rubber material during said heating thereof.

7. A product including a polyurethane bonded to a silicone rubber material obtained by the method of claim 1.

8. A method for applying a silicone rubber material to a polyurethane surface, comprising:
   supplying a base material having an exposed surface which includes a polyurethane;
   applying a silicone rubber material to said base material, said silicone rubber material being an acetoxyterminated siloxane, a halogen-terminated siloxane or a combination thereof, said acetoxy and said halogen moieties are bonded to a silicon in said rubber material;
   heating said base material at a temperature above about 70° C. to condition said base material to bond said silicone rubber material to said polyurethane; and
   whereby said heating of at least said base material provides a bond between said silicone rubber material and said polyurethane which is stronger than a bond which occurs between said polyurethane and said silicone rubber material in the absence of said heating step.

9. The method as defined in claim 8 wherein said silicone rubber material is applied to said base material as a solution consisting essentially of about 10% by weight of said silicone rubber material and a solvent, said solvent being formulated as a blend of about 90% fluorinated hydrocarbon and about 10% 1,1,1-trichloroethane.

10. The method as defined in claim 8 wherein said heating of said base material and said silicone rubber material is carried out at a temperature between about 100° C. and about 130° C. for a period of time between about 0.5 minutes and about 15 minutes.

11. The method as defined in claim 8 wherein said curing of said silicone rubber material is accomplished during said heating of said base material and said silicone rubber material.

12. The method as defined in claim 8 further comprising:
   blowing air on said base material and said silicone rubber material during said heating thereof.

13. A product including a polyurethane bonded to a silicone rubber material obtained by the method of claim 9.

14. The method as defined in claim 8 wherein said heating of at least said base material is accomplished by heating above the second glass transition temperature of said polyurethane.

15. In a method for applying a solution containing a silicone rubber material to a polyurethane to bond the silicone rubber material to the polyurethane, the improvement comprising:
   heating a polyurethane material at a temperature above about 70° C. to bond the silicone rubber material to said polyurethane, said heating of said polyurethane, said heating of said polyurethane providing a bond between said silicone rubber material and said polyurethane which is stronger than a bond between said polyurethane and said silicone rubber material which occurs in the absence of said heating step, said silicone rubber material being an acetoxy-terminated siloxane, a halogen-terminated siloxane or a combination thereof, said acetoxy and halogen moieties being bonded directly to silicon in said rubber materials; and blowing hot air on said base material and said rubber material during said heating step.

16. The method as defined in claim 15 wherein said silicone rubber material is applied to said base material as a solution consisting essentially of about 10% by weight of said silicone rubber material in a solvent, said solvent being formulated as a blend of about 90% fluorinated hydrocarbon and about 10% 1,1,1-trichloroethane.

17. The method as defined in claim 15 wherein said heating of said base material and said silicone rubber material is carried out at a temperature between about 100° C. and about 130° C. for a period of time between about 0.5 minutes and about 15 minutes.

18. A product including a polyurethane bonded to a silicone rubber material obtained by the method of claim 15.

19. The method as defined in claim 15 wherein said heating of said polyurethane material is accomplished by heating above the second glass transition temperature of said polyurethane.

* * * * *